(12) United States Patent
Veglio et al.

(10) Patent No.: US 8,314,285 B2
(45) Date of Patent: Nov. 20, 2012

(54) PANTILINER

(75) Inventors: Paolo Veglio, Pescara (IT); Ivano Gagliardi, Pescara (IT); Giovanni Carlucci, Chieti (IT); Roberto D'Addario, Pianella (IT); Vincenzo Partenza, Elice (IT)

(73) Assignee: The Procter and Gamble Company, Cincinnati, OH (US)

( * ) Notice: Subject to any disclaimer, the term of this patent is extended or adjusted under 35 U.S.C. 154(b) by 1283 days.

(21) Appl. No.: 10/790,418

(22) Filed: Mar. 1, 2004

(65) Prior Publication Data

US 2005/0192549 A1    Sep. 1, 2005

(51) Int. Cl.
*A61F 13/53* (2006.01)
*A61F 13/472* (2006.01)
*A61F 13/537* (2006.01)

(52) U.S. Cl. .................................. 604/367; 604/385.31
(58) Field of Classification Search .................. 604/385, 604/367, 385.101, 385.31
See application file for complete search history.

(56) References Cited

U.S. PATENT DOCUMENTS

| | | | | |
|---|---|---|---|---|
| 2,905,176 A | * | 9/1959 | Davidson | 604/371 |
| 2,964,040 A | * | 12/1960 | Morse et al. | 604/366 |
| 3,559,650 A | * | 2/1971 | Larson | 604/364 |
| 3,612,054 A | * | 10/1971 | Matsuda et al. | 604/370 |
| 3,871,378 A | * | 3/1975 | Duncan et al. | 604/372 |
| 4,041,951 A | * | 8/1977 | Sanford | 604/375 |
| 4,195,634 A | * | 4/1980 | DiSalvo et al. | 604/366 |
| 4,324,246 A | * | 4/1982 | Mullane et al. | 604/366 |
| 4,341,217 A | * | 7/1982 | Ferguson et al. | 604/385.08 |
| 4,342,314 A | * | 8/1982 | Radel et al. | 604/370 |
| 4,397,644 A | * | 8/1983 | Matthews et al. | 604/378 |
| 4,463,045 A | * | 7/1984 | Ahr et al. | 428/131 |
| 4,681,578 A | | 7/1987 | Anderson | |
| 4,713,069 A | * | 12/1987 | Wang et al. | 604/378 |
| 4,738,676 A | | 4/1988 | Osborn, III | |
| 4,781,711 A | * | 11/1988 | Houghton et al. | 604/378 |
| 4,798,603 A | * | 1/1989 | Meyer et al. | 604/378 |
| 5,217,445 A | * | 6/1993 | Young et al. | 604/381 |
| 5,234,422 A | * | 8/1993 | Sneller et al. | 604/385.25 |

(Continued)

FOREIGN PATENT DOCUMENTS

EP    0 555 346 B1    5/1996

(Continued)

OTHER PUBLICATIONS

Lewis, Richard J., Sr., Hawley's Condensed Chemical Dictionary, 1997, John Wiley & Sons, Inc., 13th Ed., pp. 897-898.*

(Continued)

*Primary Examiner* — Melanie Hand
*Assistant Examiner* — Paula Craig
(74) *Attorney, Agent, or Firm* — Megan C. Hymore; Jason J. Camp; Roddy M. Bullock

(57) ABSTRACT

A sanitary napkin comprising a fluid permeable topsheet, a fluid permeable backsheet, and an absorbent core disposed therebetween is disclosed. The sanitary napkin can be a pantiliner. The absorbent core comprises relatively hydrophilic material defining a core outer periphery. The topsheet and the backsheet comprise relatively hydrophobic nonwoven material, at least one of the topsheet and the backsheet defining a sanitary napkin outer periphery that is substantially larger than the core outer periphery. The area between the core outer periphery and the sanitary napkin outer periphery is a breathable zone. The sanitary napkin further comprises a fluid impermeable barrier between the backsheet and the absorbent core, the fluid impermeable barrier being disposed within the core outer periphery.

19 Claims, 1 Drawing Sheet

U.S. PATENT DOCUMENTS

| | | | | |
|---|---|---|---|---|
| 5,368,909 A | * | 11/1994 | Langdon et al. | 428/137 |
| 5,549,589 A | * | 8/1996 | Horney et al. | 604/366 |
| 5,599,334 A | | 2/1997 | Johnston et al. | |
| 5,603,707 A | * | 2/1997 | Trombetta et al. | 604/383 |
| 5,609,588 A | * | 3/1997 | DiPalma et al. | 604/369 |
| 5,658,639 A | * | 8/1997 | Curro et al. | 428/131 |
| 5,728,084 A | | 3/1998 | Palumbo et al. | |
| 5,762,642 A | * | 6/1998 | Coles et al. | 604/378 |
| 5,800,418 A | * | 9/1998 | Ahr | 604/368 |
| 5,807,363 A | * | 9/1998 | Hamajima et al. | 604/366 |
| 5,843,066 A | * | 12/1998 | Dobrin | 604/385.21 |
| 5,961,509 A | * | 10/1999 | Kling | 604/385.03 |
| 6,142,983 A | * | 11/2000 | Suprise et al. | 604/385.03 |
| 6,232,521 B1 | * | 5/2001 | Bewick-Sonntag et al. | 604/378 |
| 6,492,574 B1 | * | 12/2002 | Chen et al. | 604/378 |
| 6,582,411 B1 | * | 6/2003 | Carstens et al. | 604/385.01 |
| 6,624,341 B1 | | 9/2003 | Depner et al. | |
| 6,646,179 B1 | * | 11/2003 | Melius et al. | 604/368 |
| 6,852,905 B2 | * | 2/2005 | Baker | 604/369 |
| 6,881,206 B2 | * | 4/2005 | Underhill et al. | 604/385.101 |
| 2001/0041877 A1 | | 11/2001 | Canuel | |
| 2002/0031968 A1 | * | 3/2002 | Hamaguchi et al. | 442/402 |
| 2003/0187417 A1 | * | 10/2003 | Kudo et al. | 604/379 |
| 2005/0148964 A1 | * | 7/2005 | Chambers et al. | 604/367 |

FOREIGN PATENT DOCUMENTS

| | | |
|---|---|---|
| EP | 0 903 134 A1 | 3/1999 |
| EP | 1 040 799 A1 | 10/2000 |

OTHER PUBLICATIONS

PCT International Search Report dated Jan. 7, 2005.

* cited by examiner

PANTILINER

FIELD OF THE INVENTION

This invention relates to disposable absorbent devices and more particularly to such devices intended for use by women, such as sanitary napkins, pantiliners and the like.

BACKGROUND OF THE INVENTION

Sanitary napkins are used by women principally during their menstrual periods to receive and contain menses and other vaginal discharges to protect their garments from soiling. Sanitary napkins typically have adhesive attachment means to temporarily adhere the device to the crotch region of the user's undergarment, normally her panty.

Pantiliners serve much the same purpose as sanitary napkins; the distinction is primarily in the overall size, including thickness. Pantiliners are generally less bulky and are designed to protect the user's clothing from relatively small quantities of vaginal discharges.

Many women have developed the habit of wearing an absorbent device between their menstrual periods to protect their clothing from any vaginal discharges, including light urinary discharge, and sometimes anal discharge. Because a sanitary napkin is generally too bulky for constant wear, such user's generally utilize pantiliners.

Most pantiliners have a non-breathable backing layer, commonly referred to as a backsheet. The backsheet of typical pantiliners can be a fluid impermeable polymer film, for example. A fluid impermeable layer prevents fluids absorbed into the device from wetting through to the user's garments. However, the fluid impermeable layer also makes the pantiliner hot and uncomfortable, due to trapped moisture in the absorbent core.

Pantiliners are also known to provide a breathable backing layer, such as a breathable polymer film or nonwoven web backing layer. Generally, such backing layers are fluid impermeable, vapor permeable layers that allow the exchange of vapor while preventing the soiling of the user's garments. For example, U.S. Pat. No. 4,059,114 issued to Richards on Nov. 22, 1977, discloses a disposable garment shield having a moisture barrier ply constructed of a blown microfiber web which is fluid impermeable but vapor permeable. Also, U.S. Pat. No. 4,681,578 issued to Anderson et al. on Jul. 21, 1987 discloses an absorbent article such as a pantiliner provided with at least one ventilation area which allows the passage of vapor to provide cooling and drying effects so that the pantiliner is more comfortable to wear.

While these breathable pantiliners do provide some measure of improvement over the more common impermeable pantiliners, comfort, garment soiling, dryness, and vapor exchange (breathability) remain as key design considerations. Accordingly, absorbent devices providing for the better retention and absorption of liquids while providing for the more efficient passage of vapor have been sought.

SUMMARY OF THE INVENTION

A sanitary napkin comprising a fluid permeable topsheet, a fluid permeable backsheet, and an absorbent core disposed therebetween is disclosed. The sanitary napkin can be a pantiliner. The absorbent core comprises relatively hydrophilic material defining a core outer periphery. The topsheet and the backsheet comprise relatively hydrophobic nonwoven material, at least one of the topsheet and the backsheet defining a sanitary napkin outer periphery that is substantially larger than the core outer periphery. The area between the core outer periphery and the sanitary napkin outer periphery is a breathable zone. The sanitary napkin further comprises a fluid impermeable barrier between the backsheet and the absorbent core, the fluid impermeable barrier being disposed within the core outer periphery.

In one embodiment, the sanitary napkin is a thin absorbent pantiliner comprising a fluid permeable topsheet, a fluid permeable backsheet, and an absorbent core disposed therebetween, wherein: (a) the absorbent core has a basis weight of between about 50 gsm and 100 gsm, with the absorbent core comprising relatively hydrophilic airlaid nonwoven material having at least about 5 wt % AGM fiber content and defining a core outer periphery; and (b) the topsheet and the backsheet comprise relatively hydrophobic fluid repellent spunbonded nonwoven material, with the topsheet and the backsheet defining a pantiliner outer periphery that is larger than the core outer periphery, and with the area between the core outer periphery and the pantiliner outer periphery being a breathable zone that completely surrounds the core outer periphery, such that vapors can permeate completely through said pantiliner in the breathable zone. The pantiliner further comprises a fluid impermeable barrier between said backsheet and said absorbent core, said fluid impermeable barrier being a polyethylene film disposed adjacent to said core and within said core outer periphery and not extending beyond said core outer periphery.

DETAILED DESCRIPTION OF THE INVENTION

Figure 1:
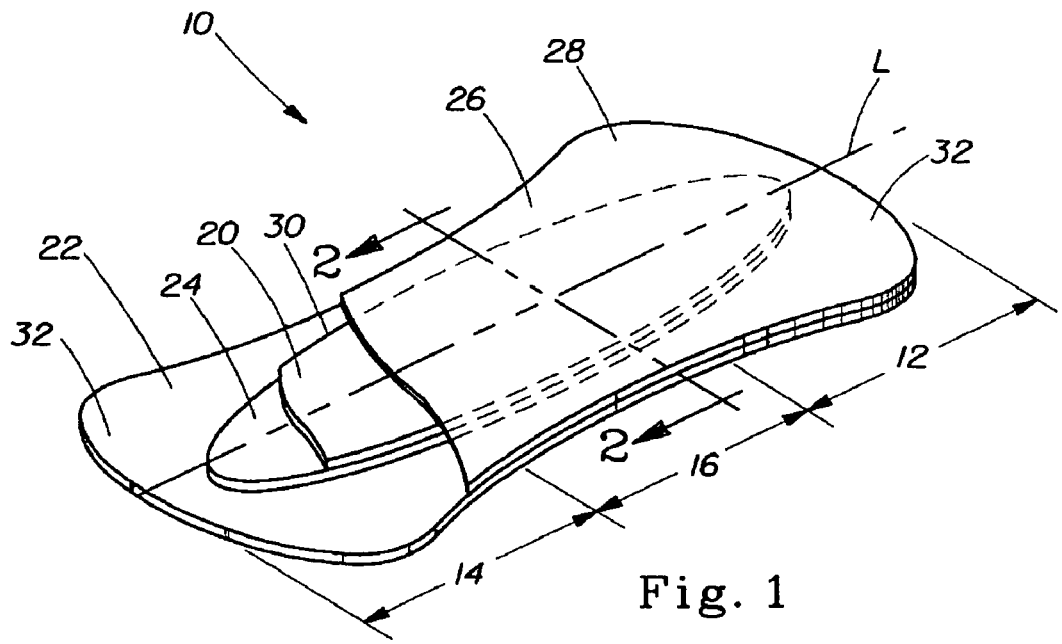
FIG. 1 is a partially cut away perspective view of a pantiliner of the present invention.
Figure 2A:
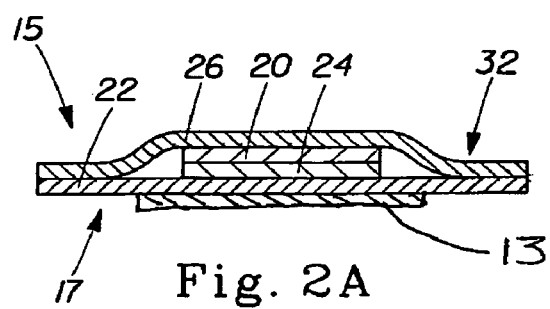
FIG. 2A is a cross-sectional view of the cross section 2-2 in on one embodiment of a pantiliner as shown in FIG. 1.
Figure 2B:
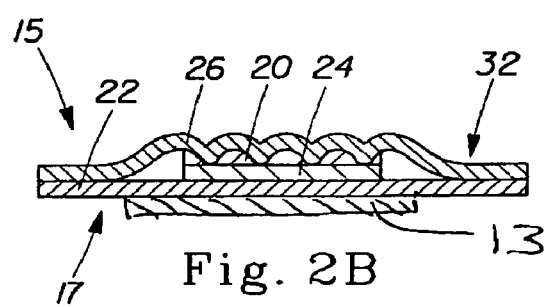
FIG. 2B is a cross-sectional view of the cross section 2-2 in another embodiment of a pantiliner as shown in FIG. 1.

A preferred embodiment of an absorbent article of the present invention, a sanitary napkin which can be a pantiliner 10 is shown in partially cut-away perspective view in FIG. 1 and cross section in FIGS. 2A and 2B. While the invention is disclosed in a particularly preferred embodiment of a pantiliner, the described invention can also be considered as a sanitary napkin, and all descriptions below with respect to pantiliners can be sanitary napkins as well, with the difference being one of degree rather than kind. The invention can also be an adult incontinence device, an anal discharge pad, an interlabial pad, or the like.

The pantiliner has two end regions 12 and 14 and a middle region 16. The pantiliner 10 has a body-facing side 15 that is in contact with the use's body and a garment facing 17 side that is in contact with the inner surface of the user' undergarment. The garment facing side 17 can have thereon pressure sensitive adhesive 13 for affixing to a wearer's undergarments. Typically, such adhesive is covered with a release strip which is removed before affixing to the undergarment.

While the pantiliner 10 may have any shape known in the art, a preferred shape is generally "hourglass" shaped, tapering inwardly from a relatively greater transverse width in a portion of one of the end regions to a relatively smaller transverse width at the middle region. Transverse width is generally defined as the dimension perpendicular to the dimension, which is defined as length, running from end region 12 to end region 14 parallel to longitudinal centerline L. Pantiliner can also be provided with lateral extensions known commonly in the art as "flaps" or "wings" (not shown) intended to extend over and cover the panty elastics in the crotch region of the user's undergarment.

Pantiliner 10 has an absorbent core 20 to absorb and store bodily fluids discharged during use. Absorbent core 20 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, a web of polymeric fibers, and a blend of polymeric fibers. In a preferred embodiment, absorbent core 20 is relatively hydrophilic. By "relatively hydrophilic" is meant that the core 20 is hydrophilic with respect to the portion of the sanitary napkin 10 in the breathable zone (discussed below), which is relatively hydrophobic. Hydrophilicity can be determined by any number of means known in the art, including by reference to contact angles of fluid on a surface. In the present invention, however, what is important is relative hydrophilicity, such that surface tensions in the napkin/fluid system tend to drive fluid deposited on the sanitary napkin into the absorbent core 20.

In a preferred embodiment absorbent core 20 is relatively thin, less than about 2 mm in thickness, preferably less than about 1 mm, and more preferably less than about 0.5 mm in thickness. The absorbent core can comprise absorbent gelling materials (AGM), including AGM fibers. In a one embodiment, the absorbent core 20 is an airlaid cellulose material having a basis weight between about 50 gsm to about 100 gsm. In one embodiment the absorbent core is a 63 gsm (60 gsm airlaid+5 wt % AGM in fiber form) available from Concert GmbH, Germany, under the designation VH063.200.B001. In another embodiment the core can be an airlaid carded, nonwoven material having a basis weight between about 50 gsm and about 100 gsm. In one embodiment, the absorbent core is an 80 gsm carded airlaid nonwoven web comprising 2.2 dtex hydrophilic polypropylene fibers and 10 dtex superabsorbent fiber, available from Sandler under the name Sawabond 24-00-32.

Absorbent core 20 is cut to a shape, the outer edges of which define a core periphery 30. The shape of absorbent core 20 can be generally rectangular, circular, oval, elliptical, or the like. Absorbent core 20 can be generally centered with respect to the longitudinal centerline L and transverse centerline T.

To provide a degree of softness and vapor permeability for the garment-facing side of pantiliner 10, a vapor permeable outer layer, referred to herein as backsheet 22, is provided adjacent the absorbent core 20 on the garment-facing side of the absorbent core 20. The backsheet 22 can be formed from any vapor permeable material known in the art. Backsheet 22 can be a microporous film, an apertured formed film, or other polymer film that is vapor permeable, or rendered to be vapor permeable, as is known in the art. A preferred material is a soft, smooth, compliant, liquid and vapor pervious material, such as a nonwoven web. A nonwoven web provides for softness and conformability for comfort, and is low noise producing so that movement does not cause unwanted sound.

In a preferred embodiment, backsheet 22 is a nonwoven web having a basis weight between about 20 gsm and about 50 gsm. In one embodiment the backsheet is a relatively hydrophobic 23 gsm spunbonded nonwoven web of 4 denier polypropylene fibers available from Fiberweb Neuberger, under the designation F102301001.

To provide for softness next to the body, pantiliner 10 can have a body-facing layer, referred to herein as topsheet 26. Topsheet 26 can be formed by any soft, smooth, compliant, porous material which is comfortable against human skin and through which vaginal discharges can pass. Topsheet 26 can comprise fibrous nonwoven webs and can comprise fibers as are known in the art, including bicomponent and shaped fibers. In one embodiment, is a relatively hydrophobic 15 gsm spunbonded nonwoven web comprising bicomponent fibers of the sheath core type (PP/PE) available from Pegas a.s., Czech Republic, under the designation 10XXN008005.

In a preferred embodiment, both topsheet 26 and backsheet 22 are hydrophobic, fluid permeable nonwoven webs. If hydrophobic, or rendered hydrophobic, such that a drop of fluid makes a contact angle of at least about 75 degrees with respect to the surface of the web, the nonwoven can be fluid repellent, thereby functioning as a liquid barrier although it is, in fact, liquid permeable.

At least one, and preferably both, of topsheet 26 and backsheet 22 define a shape, the edge of which defines an outer periphery 28 of the pantiliner. In a preferred embodiment, both topsheet 26 and backsheet 22 define the pantiliner (or sanitary napkin) outer periphery 28. The two layers can be die cut, for example, after combining all the components into the structure of the pantiliner as described herein.

Interposed between the absorbent core 20 and backsheet 22 is a fluid impermeable barrier layer 24. Barrier layer 24 prevents fluids retained by the absorbent core 20 from striking through the pantiliner and soiling adjacent garments. However, unlike prior art products, barrier layer 24 does not extend to the outer periphery 28 of the pantiliner 10. Rather, barrier layer does not extend laterally beyond core periphery 30. In a preferred embodiment, the barrier layer 24 covers completely the garment-facing side of absorbent core 20, but does not extend beyond core periphery 30.

In a preferred embodiment, absorbent core 20 does not extend laterally outward to the same extent as either topsheet 26 or backsheet 22, but the sanitary napkin outer periphery 28 is substantially larger than the core outer periphery 30. In this manner, the region of pantiliner 10 between the core periphery 30 and the sanitary napkin outer periphery 28 defines a breathable zone 32 comprising only the topsheet and/or the backsheet 22. In a preferred embodiment, the breathable zone 32 extends laterally from the core periphery 30 to and including sanitary napkin outer periphery 28. A minimum level of breathability is achieved by the use of porous nonwoven materials for the topsheet and/or backsheet. If the breathable zone comprises both the topsheet and the backsheet, it can also comprise means for joining the two, such as adhesive means, including hot melt adhesives. In such an embodiment the adhesive should not be applied so as to render the topsheet and/or backsheet completely non-porous. In one embodiment, the adhesive is put on as a series of spirals in the breathable zone.

A benefit of having a breathable zone between absorbent core periphery 30 and sanitary napkin outer periphery 28 is enabling more effective coverage of the wearer's undergarment without increasing overall bulk of the article. That is, by concentrating the absorbent core 20 to a relatively small central region of the sanitary napkin, bulk is reduced. By having a hydrophobic, breathable region surrounding the absorbent core, the garment-facing side of the sanitary napkin backsheet 22 has more surface area available for adhesive attachment to be adhered to the undergarment.

In one embodiment, the absorbent core 20 is located symmetrically with respect to the longitudinal centerline L, but placed more toward one of either the first end region 12 or second end region 14. In this manner, more of the breathable zone 32 can be disposed over the anal region of the wearer, for example.

The greatest length dimension of sanitary napkin 10 as measured parallel to the longitudinal axis L can be at least about 6 cm, or at least about 10 cm, or at least about 15 cm, or at least about 20 cm, or at least about even 25 cm or more for coverage of the anal region of the body in addition to the vaginal region. The greatest width dimension of sanitary napkin 10 as measured parallel to the transverse axis T can be at least about 3 cm, or at least about 6 cm, or at least about 10 cm. In a preferred embodiment, sanitary napkin 10 is generally hour-glass shaped having a minimum width dimension of about 5 cm in the middle, and a maximum width dimension at the end regions of about 6.5 cm, and a length dimension of about 15 cm.

The maximum surface area (i.e., the area of the sanitary napkin when viewed in flat, plan view) of the sanitary napkin 10 and absorbent core 20 is limited only by the intended use, including the relative size of a wearer's undergarments. For use as a pantiliner the sanitary napkin can cover an area of at least about 60 cm$^2$, or at least about 75 cm$^2$, preferably at least about 90 cm$^2$, and can be at least about 100 cm$^2$. Likewise, the absorbent core 20 can cover an area of at least about 20 cm$^2$, or at least about 25 cm$^2$, or at least about 35 cm$^2$ and can be at least about 45 cm$^2$ or more. In one embodiment, the breathable zone 32 represents at least about 25% of the overall surface area of the sanitary napkin. The breathable zone can represent at least about 35%, 40%, 50%, 75% or 90% of the surface area of the sanitary napkin. In one embodiment of a pantiliner of the present invention, absorbent core 20 has a surface area of about 32 cm$^2$ and the breathable zone has surface area of about 50 cm$^2$, for an overall pantiliner surface area of about 82 cm$^2$.

All the components can be adhered together with adhesives, including hot melt adhesives, as is known in the art. The adhesive can be Findlay H2128 UN and Savare' PM 17 can be applied using Dynafiber HTW system. As mentioned above, the only requirement is that the adhesive used in the breathable zone not render the breathable zone non-breathable, i.e., not render either the topsheet or backsheet non-porous. Other benefits of keeping the breathable zone porous includes preventing the sanitary napkin from sticking to the skin of the wearer, thereby increasing discomfort.

In a preferred embodiment, both the topsheet 26 and backsheet 22 have body-facing surfaces that are hydrophobic, or rendered to be hydrophobic. By hydrophobic is meant that a drop of water placed on the surface does not readily wet out and into the nonwoven. In one embodiment, the hydrophobic body-facing surface is fluid repellent, such that a drop of water placed thereon remains on the surface for an extended period of time, for example 10 to 30 minutes.

In one embodiment, the breathable zone 32 comprises both the topsheet 26 and backsheet 22 but the topsheet is very low basis weight, such that, even though it is relatively hydrophobic, fluid deposited on the portion of the topsheet overlying the relatively hydrophilic absorbent core 20 is readily drawn through the topsheet and into the absorbent core. However, fluid deposited outside of the region overlying the absorbent core, i.e., in the breathable zone 32, does not get absorbed, and does not strike through to the garment facing side of pantiliner 10.

Therefore, in use, the pantiliner 10 of the present invention provides for a very thin, flexible, comfortable pantiliner having a relatively small centrally-disposed hydrophilic "pocket" surrounded by a fluid repellent breathable zone 32. The relatively hydrophobic breathable zone acts as an effective barrier to fluid movement out of the region of the absorbent core 20. Thus, in use, fluid discharged from the body can be quickly absorbed, and prevented from running off the pantiliner and onto the user's garments.

In a preferred embodiment, breathable zone 32 completely surrounds absorbent core 20. That is, in no portion of pantiliner 10 does the core periphery 30 coincide with sanitary napkin periphery 28, but the two peripheries are always separated by a region of breathable zone 32. In this embodiment, the breathable zone 32 is a continuous band of breathable zone that completely encircles, or surrounds, absorbent core 20.

In order to promote faster fluid entry into the absorbent core 20 the topsheet 26 and absorbent core 20 can be processed so as to have a certain amount of fiber entanglement. Entanglement can be accomplished by mechanical means known in the art. For example, as shown in cross-section in FIG. 2B, the absorbent core 20 and the topsheet 26 can be entangled by embossing, such that fibers of the topsheet 26 are forced into fibers of absorbent core 20. Other means, including mechanical treatment means known in the art, such as what is commonly referred to as "ring rolling" can also be used to accomplish fiber entanglement. It is believed that fiber deformation-inducing treatments, such as embossing, not only helps expose deposited fluid to hydrophilic fibers in the absorbent core, it also forms small-scale "hills" and "valleys" that help contain deposited fluid on the pantiliner over the "pocket" of the hydrophilic absorbent core 20.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin having a body-facing side and a garment-facing side, the sanitary napkin comprising a fluid permeable topsheet, a fluid permeable backsheet, and an absorbent core disposed therebetween, wherein,
    a. said absorbent core comprises relatively hydrophilic material defining a core outer periphery;
    b. said topsheet and said backsheet comprise relatively hydrophobic nonwoven material, at least one of said topsheet and said backsheet defining a sanitary napkin outer periphery that is substantially larger than said core outer periphery, the area between said core outer periphery and said sanitary napkin outer periphery being a breathable zone that completely surrounds said core outer periphery;
    c. said sanitary napkin further comprising a fluid impermeable barrier between said backsheet and said absorbent core, said fluid impermeable barrier being disposed within said core outer periphery and not extending beyond said core outer periphery, and
    d. wherein said garment-facing side has thereon pressure sensitive adhesive for affixing to a wearer's undergarment.

2. The sanitary napkin of claim 1, wherein at least one of said topsheet and said backsheet has sufficient hydrophobicity as to be rendered fluid repellent.

3. The sanitary napkin of claim 1, wherein said topsheet and said backsheet have a common outer periphery.

4. The sanitary napkin of claim 1, wherein the periphery of said fluid impermeable barrier coincides with said core outer periphery.

5. The sanitary napkin of claim 1, wherein said topsheet and said core are joined by mechanical entangling of a portion of their respective fibers.

6. The sanitary napkin of claim 1, wherein said core outer periphery defines a generally oval shape.

7. The sanitary, napkin of claim 1, wherein said sanitary napkin periphery defines a generally hour-glass shape.

8. The sanitary napkin of claim 1, wherein said topsheet and said absorbent core are embossed to expose and entangle fibers from said core with said topsheet.

9. The sanitary napkin of claim 1, wherein said topsheet comprises a spunbonded nonwoven web.

10. The sanitary napkin of claim 9, wherein said topsheet comprises bicomponent fibers.

11. The sanitary napkin of claim 1, wherein said backsheet comprises a spunbonded nonwoven web.

12. The sanitary napkin of claim 11, wherein said backsheet comprises polypropylene fibers.

13. The sanitary napkin of claim 1, wherein said absorbent core comprises superabsorbent material.

14. The sanitary napkin of claim 13, wherein said superabsorbent material comprises superabsorbent fibers.

15. The sanitary napkin of claim 1, wherein said core comprises a carded airlaid web.

16. The sanitary napkin of claim 1, wherein said sanitary napkin is a pantiliner.

17. A sanitary napkin comprising a fluid permeable topsheet, a fluid permeable backsheet, and an absorbent core disposed therebetween, wherein,
   a. said absorbent core comprises relatively hydrophilic airlaid nonwoven material having fibrous AGM and defining a core outer periphery;
   b. said topsheet and said backsheet comprise relatively hydrophobic spunbonded nonwoven material, said topsheet and said backsheet defining a sanitary napkin outer periphery that is larger than said core outer periphery, the area between said core outer periphery and said sanitary napkin outer periphery being a breathable zone that completely surrounds the core outer periphery, such that vapors can permeate completely through said sanitary napkin in said breathable zone;
   c. said sanitary napkin further comprising a fluid impermeable barrier between said backsheet and said absorbent core, said fluid impermeable barrier being disposed adjacent to said absorbent core and within said core outer periphery and not extending beyond said core outer periphery.

18. The sanitary napkin of claim 17, wherein said sanitary napkin is a pantiliner.

19. A thin absorbent pantiliner comprising a fluid permeable topsheet, a fluid permeable backsheet, and an absorbent core disposed therebetween, wherein,
   a. said absorbent core has a basis weight of between about 50 gsm and 100 gsm, said absorbent core comprising relatively hydrophilic airlaid nonwoven material having at least about 5 wt % AGM fiber content and defining a core outer periphery;
   b. said topsheet and said backsheet comprise relatively hydrophobic fluid repellent spunbonded nonwoven material, said topsheet and said backsheet defining a pantiliner outer periphery that is larger than said core outer periphery, the area between said core outer periphery and said pantiliner outer periphery being a breathable zone that completely surrounds the core outer periphery, such that vapors can permeate completely through said pantiliner in said breathable zone;
   c. said pantiliner further comprising a fluid impermeable barrier between said backsheet and said absorbent core, said fluid impermeable barrier being a polyethylene film disposed adjacent to said core and within said core outer periphery and not extending beyond said core outer periphery.

* * * * *